United States Patent [19]

Siess

[11] 4,238,672
[45] Dec. 9, 1980

[54] TEMPERATURE CONTROL CIRCUITRY

[75] Inventor: Hans Siess, Owingen, Fed. Rep. of Germany

[73] Assignee: Bodenseewerk Perkin-Elmer & Co. GmbH, Überlingen, Fed. Rep. of Germany

[21] Appl. No.: 869,495

[22] Filed: Jan. 16, 1978

[30] Foreign Application Priority Data

Feb. 9, 1977 [DE] Fed. Rep. of Germany ....... 2705308

[51] Int. Cl.³ .............................................. H05B 1/02
[52] U.S. Cl. .................................... 219/502; 219/497; 219/501; 219/488; 219/514; 236/15 BB; 236/DIG. 15
[58] Field of Search ............... 219/483, 272, 380, 502, 219/494, 497, 499, 501, 510, 488; 236/78 D, 8, 15 BB, 15 BF, DIG. 15

[56] References Cited

U.S. PATENT DOCUMENTS

| | | | |
|---|---|---|---|
| 1,626,663 | 5/1927 | Brace | 236/78 D |
| 2,404,147 | 7/1946 | Strickland, Jr. | 236/DIG. 15 |
| 2,924,695 | 2/1960 | Atkeson | 236/15 BF X |
| 3,330,940 | 7/1967 | Hocker | 219/510 X |
| 3,781,521 | 12/1973 | Kircher | 219/494 |
| 3,808,402 | 4/1974 | Rea | 219/483 |
| 3,821,516 | 6/1974 | Hayes et al. | 219/501 |
| 3,858,141 | 12/1974 | Lackey | 219/501 |
| 3,869,597 | 3/1975 | Strange | 219/497 |

FOREIGN PATENT DOCUMENTS 839551 6/1960 United Kingdom ..................... 219/494

OTHER PUBLICATIONS

Temperature Controlled Heating of the Graphite Tube Atomizer in Flameless Atomic Absorption Spectrometry–Analytical Chemistry vol. 46 #8 pp. 1028–1031, Jul. 1974.

Primary Examiner—Bruce A. Reynolds
Assistant Examiner—Mark H. Paschall
Attorney, Agent, or Firm—Salvatore A. Giarratana; Francis L. Masselle; Edwin T. Grimes

[57] ABSTRACT

A temperature control circuit particularly for use with a graphite tube atomizer of an atomic absorption spectrometer provides rapid temperature rise and a leveling at a constant predetermined temperature. A.C. power applied through a transformer to electrodes on the ends of the graphite tube rapidly heats the tube and the visible radiation thus produced is measured by a photocell, the output of which is amplified to control a relay in the graphite tube power circuit. When the desired tube temperature is approached, the photocell output actuates the relay so that the tube power circuit will switch from the high voltage rapid heating mode to a controlled lower voltage that will automatically maintain the constant predetermined tube temperature.

6 Claims, 1 Drawing Figure

U.S. Patent
Dec. 9, 1980
4,238,672
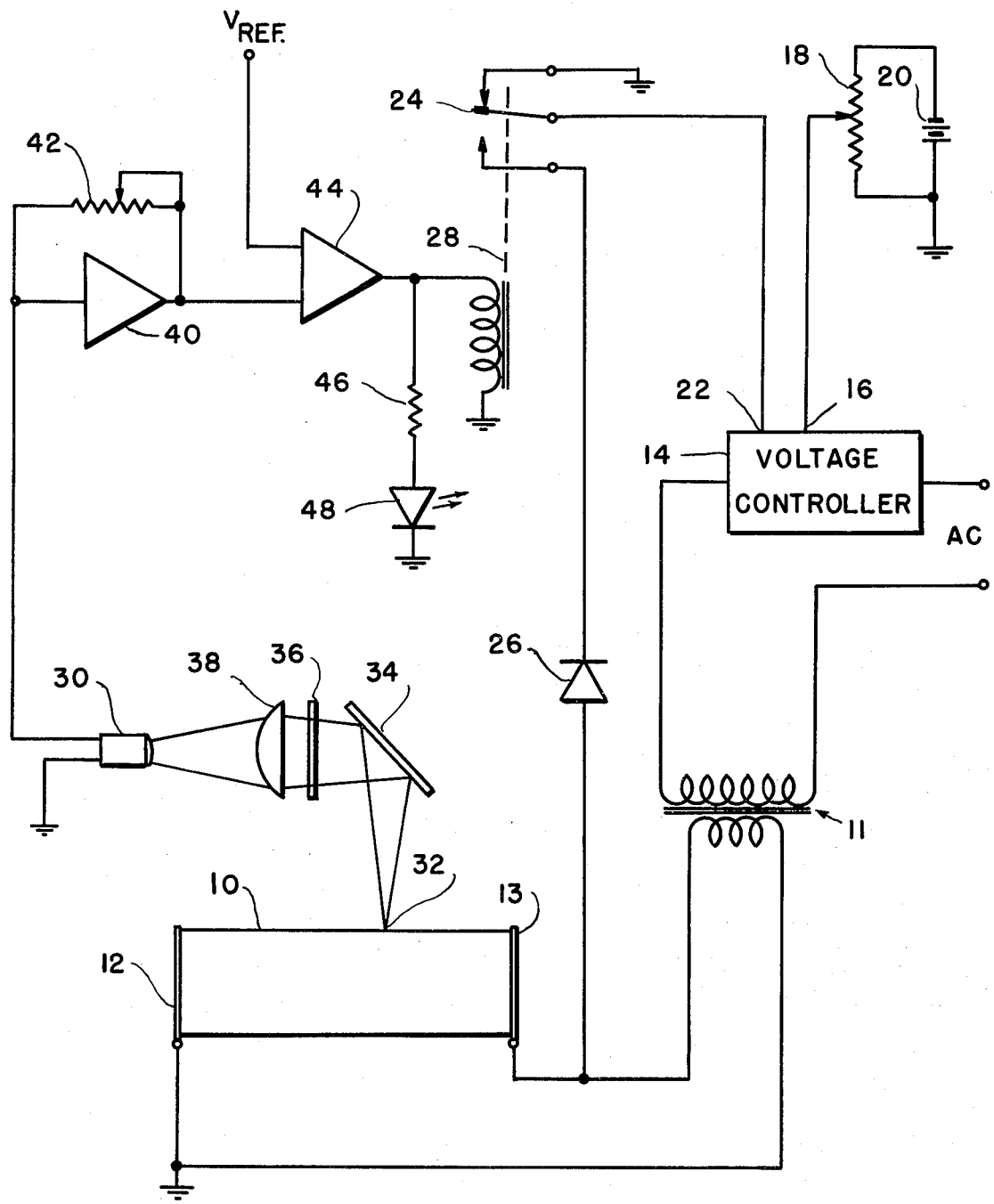

TEMPERATURE CONTROL CIRCUITRY

BACKGROUND OF THE INVENTION

In the so-called "flameless" atomic absorption measurements, a sample to be analyzed is fed into the graphite tube atomizer of an atomic absorption spectrometer. The graphite tube is mounted between annular electrodes at the ends of the tube and a control voltage is applied to produce a heating current that heats the tube to a desired high temperature while an inert gas flow to the tube prevents burning of the graphite. When the tube is sufficiently heated, usually to a temperature above 800° C., the sample in the graphite tube will be atomized to form an atomic cloud containing each of the various elements in the sample. The measuring beam of the absorption spectrometer then passes axially through the graphite tube to analyze the elements within the atomic cloud and to determine their proportional quantities by the amount of attenuation of the spectrometer beam.

Different graphite tube temperatures are required for the analysis of different samples and it is most desirable to reach the required temperature as quickly as possible so that the sample will be atomized completely as rapidly as possible. It is therefore important that a relatively high voltage be applied across the graphite tube to provide a rapid heating current and then, at the proper temperature required to atomize the contained sample, the heating current should be reduced to maintain the desired temperature. It is, of course, possible to manually switch on a higher voltage for rapid tube heating and then, as temperature approaches the desired level, manually reduce the voltage to a temperature-maintaining level. There are, however, automatic voltage adjustment systems. One said system is described in the article entitled "Temperature Controlled Heating of the Graphite Tube Atomizer in Flameless Atomic Absorption Spectrometry" by Lundgren et al, at Volume 6, No. 8, Page 1028 of "Analytical Chemistry", July 1974. That article describes a temperature-controlling circuit including a precision photodiode positioned to sense the radiation from the graphite tube surface passing through selected red filters. The output of the photodiode thus represents a particular temperature and is applied to a differential amplifier where it is compared with a reference voltage. The output of the differential amplifier controls a triac in the graphite tube primary voltage circuit so that full heating power is switched on and off as necessary to obtain and maintain a desired tube temperature. Obviously, the accuracy of this temperature control circuit depends upon the accuracy of the detector signal and aging of the detector or other variations, such as dust or other deposits on any of the optical elements, directly affect the temperature to which the graphite tube is controlled. Furthermore, the on-off control of the full heating power permits temperature over-shooting and hunting.

BRIEF SUMMARY OF THE INVENTION

The present invention includes optically controlled circuitry that permits a rapid heating of the graphite tube up to the approximate desired temperature level, and when that level is reached, transfers its control to adjustable power control circuit that regulates the tube heating voltage to automatically maintain the constant predetermined heat level for proper atomization. Since extreme accuracies are not required of the optically controlled circuitry, it preferably includes a low cost optical system that focuses a small segment of the graphite tube surface onto a low cost photodetector which is coupled through a variable gain amplifier to a comparator where the signal is compared with a reference voltage representing the desired temperature level. When the graphite tube reaches that level, the comparator outputs a signal to the coil of a relay, the SPDT contacts of which are in the graphite tube power circuit. Thus, the power circuit is initially switched by the optical circuitry controlled relay contacts to provide a high voltage across the graphite tube for rapid heating, and when the predetermined temperature is reached, the comparator signal switches over the relay and a voltage controller in the power supply circuitry provides the proper output voltage to maintain a constant, non-hunting temperature level.

DRAWING DESCRIPTION

The single drawing is a schematic diagram illustrating a preferred embodiment of the circuitry of the invention.

DETAILED DESCRIPTION OF THE PREFERRED EMBODIMENT

In the drawing, the numeral 10 designates a graphite tube of a graphite tube atomizer for an atomic absorption spectrometer. A sample to be analyzed is inserted within the bore of the tube 10 and the tube is heated by a heating current supplied by transformer 11 and applied to electrodes 12 and 13 at each end of the tube 10. The primary winding of transformer 11 is connected to a source of alternating current through a voltage controller 14 which varies the voltage to the transformer 11 in accordance with a D.C. command signal applied to the input terminal 16. The D.C. command signal is derived from a potentiometer 18 coupled across a D.C. source 20, the positive side of which is grounded and the command signal voltage represents the desired final temperature level of the tube 10. A second input terminal 22 receives a voltage control signal and is coupled to a movable arm 24 of a single pole double-throw relay 28. When relay 28 is not energized, as shown in the figure, contact 24 is grounded and voltage controller 14 applies the full A.C. voltage to the primary winding of the transformer 11. On the other hand, when relay 28 is energized, the contact 24 is coupled to the cathode of a rectifying diode 26, the anode of which is coupled to the ungrounded leg of the secondary winding of transformer 11 so that the relay contacts 24 will transmit to terminal 22 of the voltage controller 14 a signal representing the voltage across the graphite tube 10. The D.C. graphite tube signal is compared within the comparator 14 with the D.C. command signal from the potentiometer 18 and the resulting "error" signal is used in the controller 14 to regulate the A.C. voltage applied to the primary windings of transformer 11. The voltage controller 14 will thereby apply a reduced voltage to the transformer 11 to maintain a constant predetermined temperature of the graphite tube 10.

The temperature of the graphite tube 10 is pyrometrically measured using a photoelectric detector 30 which is adjusted to receive the image of a spot 32 on the surface of the graphite tube 10. Preferably, the spot 32 is reflected by a mirror 34 and through heat filter 36 and condensing lens 38 into the detector 30. It should be pointed out at this point that the only function of the optical system and its associated circuitry is to switch the graphite tube heating voltage from high level to a carefully controlled level at the approximate desired tube temperature. The photodetector 30 and its associated circuitry need not make the transfer at the precise desired temperature and therefore it follows that the components contained in the photodetector and associated circuitry need not be high-priced precision devices. Accordingly, mirror 34 may be a conventional low-cost mirror with the reflecting coating on the rear surface, and lens 38 may be a simple glass lens rather than, for example, a germanium lens as would normally be necessary for precision operation in the infrared range. Also, the photodetector 30 may be an inexpensive silicon photodiode and not necessarily precision calibrated.

The output signal generated by the detector 30 is applied to the input of an operational amplifier 40 which is gain-adjusted by a negative feed-back potentiometer 42. The output of amplifier 40 provides an input to a comparator 44, the second input of which receives a constant reference voltage. The output of the comparator 44 drives the excitation coil of the relay 28 and is also coupled through a resistor 46 and a light-emitting diode 48 to ground.

OPERATION

After a sample has been admitted to the bore of the graphite tube 10 and the A.C. power turned on, the relay 28 is in its normal non-energized condition and relay contact 24 is grounded so that the voltage controller 14 will apply a high voltage on the primary of transformer 11. The full secondary voltage is applied to the electrodes 12 and 13 to provide a very rapid heating of the graphite tube 10.

As heating of graphite tube 10 increases, its surface radiates and the resulting glow is imaged through the optical system comprising mirror 34 and lens 38 upon the photodetector 30 which generates a D.C. output signal or varies in resistance by an amount proportional to the intensity of the infrared radiation at spot 32. A fixed reference voltage applied to the comparator 44 preferably has a value that will permit an output from the comparator when the gain control of amplifier 40 is at its lowest level. Therefore, the graphite tube temperature may be adjusted to the desired level by increasing the gain of the amplifier 40 by the adjustment of potentiometer 42. When this desired graphite tube temperature level is sensed at the spot 32 by the photodetector 30, the amplified signal applied to the comparator 44 will cause the comparator to energize the relay 28 and throw the relay contact 24. Voltage controller 14 now receives the rectified voltage appearing across the graphite tube 10 and controls the voltage to maintain a constant heating current in accordance with the temperature command signal produced by potentiometer 18 across the D.C. source 20.

Prior to operation of the graphite tube control circuitry, it is advisable to properly adjust the feed-back resistor 42 so that the comparator 44 and relay 28 will change state at least approximately at the desired predetermined temperature so that the constant predetermined temperature may be accuratly maintained by adjustment of the potentiometer 18. The feed-back potentiometer 42 is adjusted in a test run by first heating the graphite tube to the desired predetermined temperature by grounding, as required, the input terminal 22 of the voltage controller 14. The feed-back resistor 42 is then adjusted to the point where the comparator 44 outputs a signal and the LED 48 begins to flicker. At this point, there is a desired matching of the feed-back resistor 42 with the desired tube temperature. The system is now ready for operation and analyses of samples may then be carried out in the normal manner.

I claim:

1. Control circuitry for controlling the application of electrical power to heating electrodes for rapidly heating and for sustaining a constant preselected elevated temperature of a member having a surface which, when heated, emits radiation, said circuity comprising:

photodetector means positioned to observe the radiation produced at the surface of the member to be heated;

adjustable threshold circuitry coupled to the output of said photodetector means, said threshold circuitry being adjustable to generate an output signal when the radiation from said member reaches a level corresponding to a first predetermined threshold temperature of said member which is in the range of said preselected elevated temperature;

voltage controller means for controlling the voltage supplied to said heating electrodes;

first input means, including switching means, for inputting into said voltage controller means a first signal indicative of the voltage supplied to said heating electrodes when said switching means is in a first position and for discontinuing said first signal when said switching means is in a second position;

said switching means being switchable from its second position to its first position by the output signal from said threshold circuitry;

second input means for inputting an adjustable command signal into said voltage controller means corresponding to the preselected elevated temperature of the member;

said voltage controller means providing a high heating first output voltage to said heating electrodes in the absence of said first input signal, and in the presence of said first input signal shifts into an automatic control mode of operation in which a second output voltage to said heating electrodes is provided corresponding to a comparison of said first input signal and said command signal.

2. The control circuitry claimed in claim 1 wherein said photodetector means includes an optical system that images a spot on the surface of said member into a photoelectric detector.

3. The control circuitry claimed in claim 2 wherein said photoelectric detector is a silicon photodiode sensitive in the visible wave length range.

4. The control circuitry claimed in claim 2 wherein the output of said photoelectric detector is amplified by a variable gain amplifier and wherein the amplified signal is compared with a fixed reference voltage, said fixed reference voltage and the variable gain of said amplifier being selected to generate a threshold output signal when said member reaches a level at and above said predetermined elevated temperature.

5. The control circuitry claimed in claim 4 further including indicating means coupled to indicate the presence or absence of said threshold output signal.

6. The control circuitry claimed in claim 5 wherein said indicating means is a light-emitting diode.

* * * * *